US00PP29674P3

(12) United States Plant Patent
Wirthensohn et al.

(10) Patent No.: US PP29,674 P3
(45) Date of Patent: Sep. 18, 2018

(54) ALMOND VARIETY NAMED 'CAPELLA'

(50) Latin Name: *Prunus dulcis*
Varietal Denomination: 'CAPELLA'

(71) Applicants: ADELAIDE RESEARCH & INNOVATION PTY LTD, Adelaide (AU); HORTICULTURE INNOVATION AUSTRALIA LIMITED, Sydney (AU)

(72) Inventors: Michelle Wirthensohn, Adelaide (AU); Andrew Granger, Montacute (AU)

(73) Assignees: Adelaide Research & Innovation Pty Ltd, Adelaide (AU); HORTICULTURE INNOVATION AUSTRALIA LIMITED, Sydney (AU)

( * ) Notice: Subject to any disclaimer, the term of this patent is extended or adjusted under 35 U.S.C. 154(b) by 0 days.

(21) Appl. No.: 14/999,565

(22) Filed: May 26, 2016

(65) Prior Publication Data

US 2017/0347510 P1 Nov. 30, 2017

(51) Int. Cl.
*A01H 5/08* (2006.01)

(52) U.S. Cl.
USPC ..... Plt./155
CPC ..... *A01H 5/0837* (2013.01)

(58) Field of Classification Search
USPC ..... Plt./155
CPC ..... A01H 5/0825; A01H 5/0837
See application file for complete search history.

*Primary Examiner* — Kent L Bell
(74) *Attorney, Agent, or Firm* — Marshall, Gerstein & Borun LLP

(57) ABSTRACT

A new and distinct almond variety of *Prunus dulcis* named 'CAPELLA', particularly characterized by self-fertility and very high production. Other desirable characteristics include early to medium harvest time, well-sealed hard shells, and high quality, sweet kernels with high oleic acid content.

3 Drawing Sheets

Latin name of the genus and species of the plant claimed: *Prunus dulcis*.

Variety denomination: 'CAPELLA'.

BACKGROUND OF THE INVENTION

The present invention relates to a new and distinct cultivar of almond varieties, botanically known as *Prunus dulcis*, and hereinafter referred to by the name 'CAPELLA'.

The disclosure provides a new and distinct variety of almond tree, botanically known as *Prunus dulcis*, synonymous with *Prunus amygdalus* Batsch., *Amygdalus communis* L., and *Amygdalus dulcis* Mill., which belongs to the Rosaceae family, and is hereinafter referred to by the variety denomination 'CAPELLA'.

The new *Prunus dulcis* variety is a product of a controlled breeding program conducted by the inventors Michelle Wirthensohn and Andrew Granger in Adelaide, Australia. The objective of the breeding program was to develop new almond varieties with high production, self-fertility and good kernel characteristics.

The new *Prunus dulcis* 'CAPELLA' originated from a cross in 1997 in Adelaide, Australia. The female or seed parent is *Prunus dulcis* variety designated 'Nonpareil' (unpatented) and the male or pollen parent is the French self-fertile *Prunus dulcis* variety designated 'Lauranne' (unpatented). The new *Prunus dulcis* 'CAPELLA' was selected by the inventors from the progeny of the stated cross in field trials in 2009 in Lindsay Point, Australia. First observations occurred in 2001.

Asexual propagation of the new *Prunus dulcis* 'CAPELLA' by grafting onto *Prunus persica* (L.) Batsch rootstock designated 'Nemaguard' (unpatented) was first performed in 2005 in the orchard located in Lindsay Point, Australia. Asexual propagation of the new *Prunus dulcis* 'CAPELLA' has confirmed that the characteristics as herein disclosed for the new variety are stable and retained through successive generations of asexual propagation. The new variety propagates true-to-type.

Asexual reproduction of the new almond tree has shown that the unique features of this new almond tree are stable and reproduced true to type in successive generations of asexual reproduction.

SUMMARY OF THE INVENTION

The 'CAPELLA' variety of almond is of medium size, medium to high vigor with slightly open growth and demonstrates very high and regular production of hardshell nuts with kernels having an excellent flavour similar to 'Nonpareil' (unpatented). The harvest maturity is slightly later than 'Nonpareil' (unpatented) and the nuts release from the hulls readily. Doubles are not produced under growing conditions in the Riverland area of South Australia. The tree is self-fertile and, therefore, is able to produce almonds without the use of pollinators.

The following traits have been repeatedly observed and are determined to be the unique characteristics which make the new variety 'CAPELLA' clearly distinguishable from its parents and the variety most similar of common knowledge which is 'Ferragnès' (unpatented):

1. self-fertility;
2. high productivity; and
3. ease of harvest.

The following characteristics listed in Table 1 have been repeatedly observed in combination and distinguish 'CAPELLA' as a new and distinct almond variety:

TABLE 1

| Trait | New variety 'CAPELLA' | Female parent 'Nonpareil' (unpatented) | Male parent 'Lauranne' (unpatented) | Most similar variety of common knowledge 'Ferragnès' (unpatented) |
|---|---|---|---|---|
| Shell type | Hard | Paper | Hard | Hard |
| Tree habit | Slightly open | Slightly open | Spreading-drooping | Upright |
| Self-fertility | Present | Absent | Present | Absent |
| Flowering time | Medium | Early-medium | Late-very late | Medium |
| Kernel size | Large | Medium | Small | Large |
| Time of maturity | Early-medium | Early | Early-medium | Very late |

Distinguishing characteristics of 'CAPELLA' are set out in Table 1. Plants of the new 'CAPELLA' almond tree have not been observed under all possible environmental conditions and cultural practices. The phenotype may vary somewhat with variations in environment, such as temperature, day length and light intensity, without, however, any variance in genotype.

The primary difference between the new variety and the female parent 'Nonpareil' (unpatented) is the new variety is self-fertile, whereas 'Nonpareil' (unpatented) is self-sterile and requires a pollinator tree planted near to fertilize the flowers and, thus, produce almonds. In comparison to its male parent 'Lauranne' (unpatented), the new variety blooms earlier by about 5-7 days, has larger fruit, and has a slightly open tree habit.

The primary difference between the new variety and the most similar variety of common knowledge 'Ferragnès' (unpatented) is the new variety is self-fertile, whereas 'Ferragnès' (unpatented) is self-sterile and requires a pollinator tree planted near to fertilize the flowers and, thus, produce almonds.

BRIEF DESCRIPTION OF THE DRAWING

The accompanying photographs (drawings) illustrate the overall appearance of the new *Prunus dulcis* 'CAPELLA' showing the colors, as true as is reasonably possible with digital reproduction. Colors in the photographs may differ slightly from the color values cited in the detailed botanical description, which accurately describe the color of 'CAPELLA'. The trees were grown on Nemaguard rootstock.

DETAILED BOTANICAL DESCRIPTION

Figure 1:
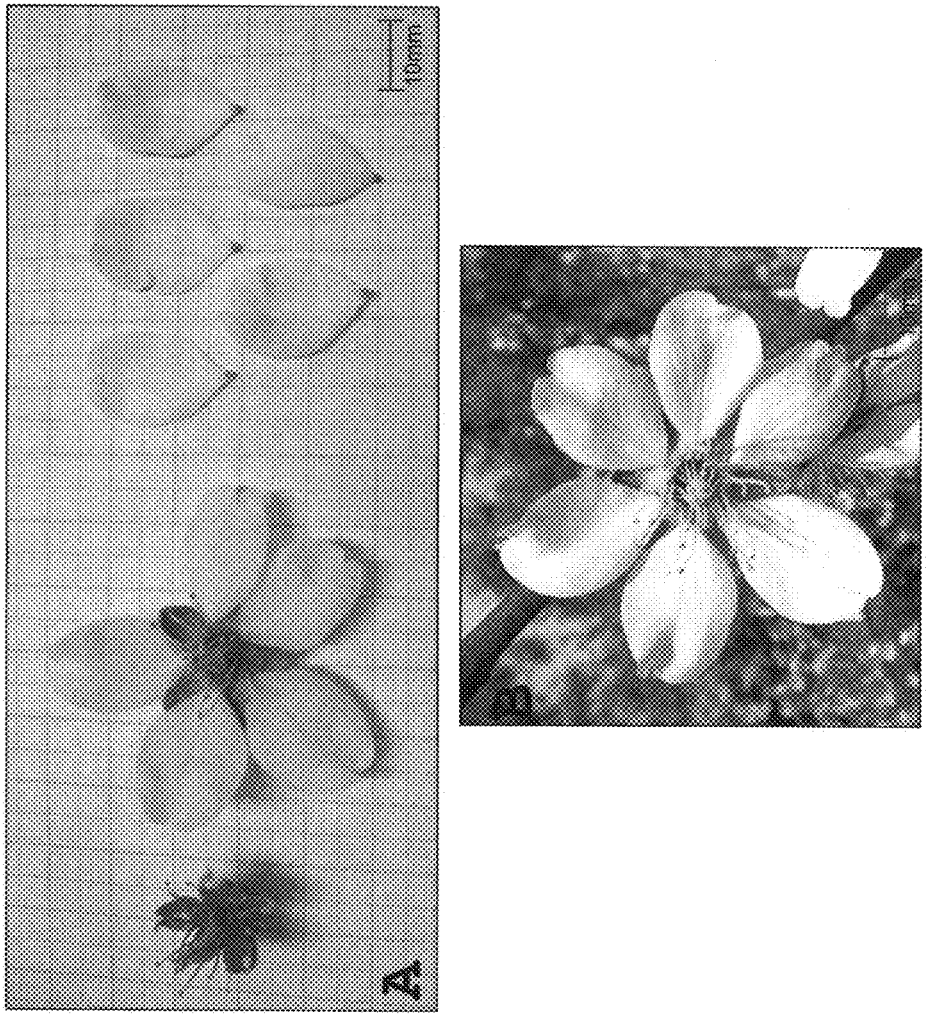
FIG. 1 shows typical flowers of 'CAPELLA', dissected (FIG. 1A) and in situ (FIG. 1B).
Figure 2:
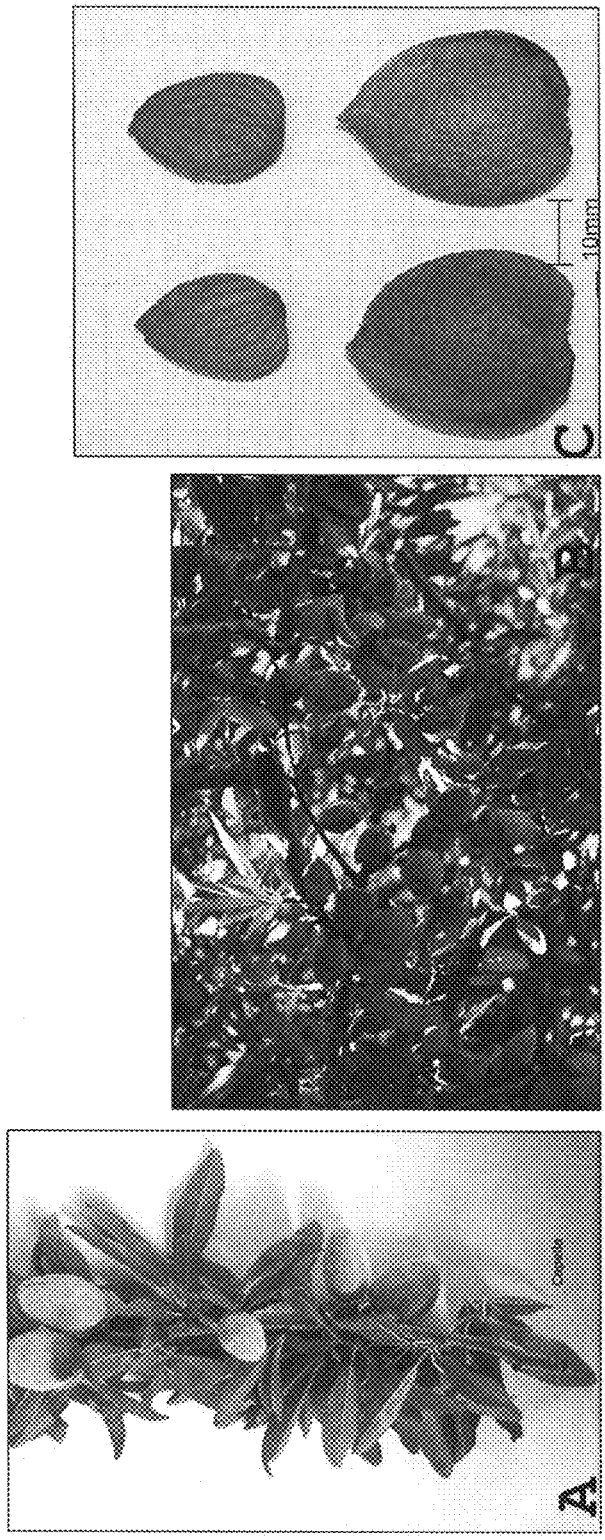
FIG. 2 shows various images of fruit of 'CAPELLA', including a one year-old shoot, showing green immature fruit (FIG. 2A), mature fruit in situ (FIG. 2B), and kernel and dry fruit shape (FIG. 2C).
Figure 3:
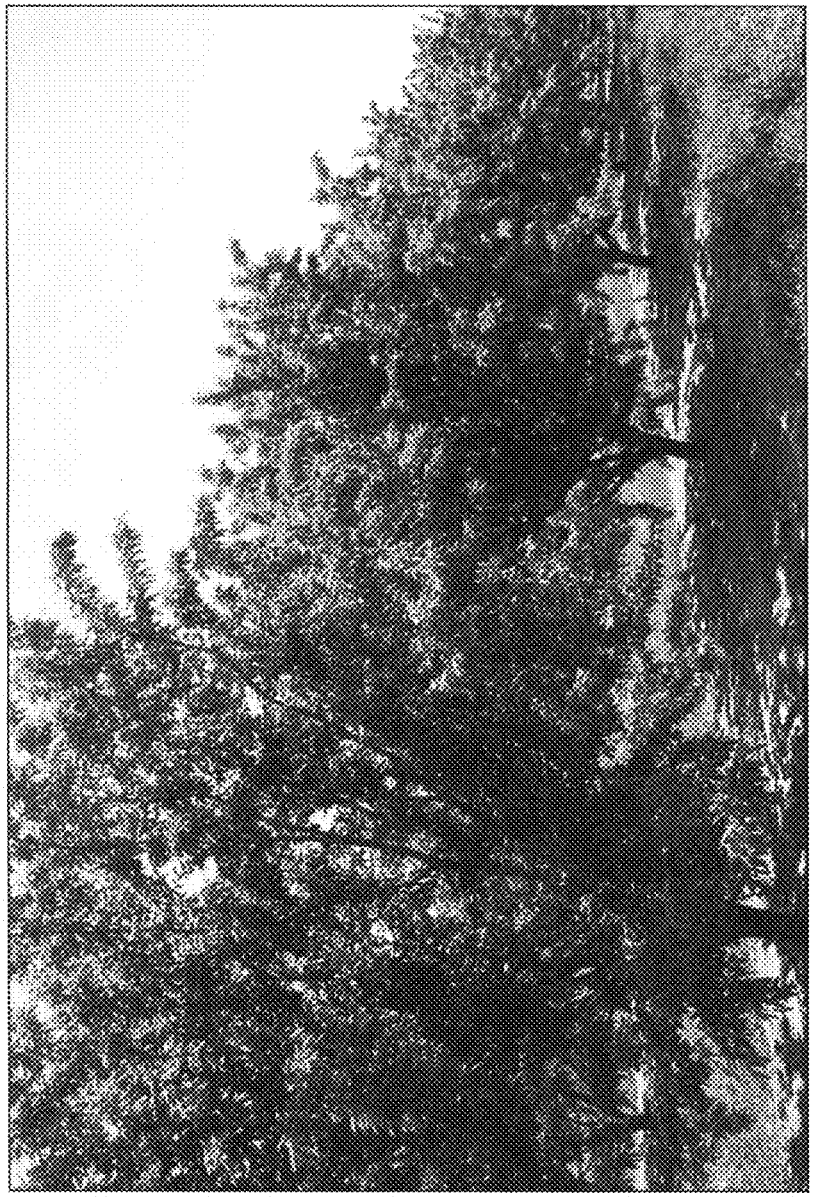
FIG. 3 shows a typical four year-old tree of 'CAPELLA' on 15 Sep. 2010.

Plants used in the aforementioned photographs and in the following description were grown outside under natural season conditions and cultural practices which approximate those generally used in commercial almond production. During the production of the plants, day temperatures ranged from about 14.5° C. to 48.2° C., night ranged from about −5.7° C. to 14° C. and light levels ranged from about 126,905 to 564,729 foot-candles. Measurements and numerical values represent averages for typical flowering plants.

The following is a detailed description of the new 'CAPELLA' variety when observed during the growing seasons from 2010 to 2015 at Lindsay Point, Victoria, Australia. During 2015, the 'CAPELLA' trees were nine years of age. Quantified measurements are expressed as an average of measurements taken from a number of trees of 'CAPELLA'. The measurements of any individual tree (or any group of trees) of 'CAPELLA' may vary from the stated average.

Color references are made to The Royal Horticultural Society Colour Chart (R.H.S.)., sixth edition, (2015). Color values were taken under conditions of natural light.

All of the trees of 'CAPELLA', insofar as they have been observed, have been consistent in the characteristics described below.

Classification:

*Botanical.*—*Prunus dulcis.*

Parentage:

*Female, or seed parent.*—*Prunus dulcis* variety designated 'Nonpareil', unpatented.

*Male, or pollen parent.*—French self-fertile *Prunus dulcis* variety designated 'Lauranne', unpatented.

Propagation:

*Type.*—Budding onto rootstock.

*Time to initiate roots.*—NA.

*Time to produce young plant.*—Eight months.

*Root description.*—'Nemaguard' (unpatented) rootstock.

Plant description:

Tree:

*Size.*—Slightly smaller than Nonpareil. Mature tree height is approximately 5.5 meters with a spread of approximately 5 meters at about 11 years of age.

*Vigor.*—Medium to high.

*Density.*—Medium to high.

*Habit.*—Slightly open.

Trunk:

*Diameter.*—About 15 cm wide and about 52.6 cm high at about 4 years of age.

*Texture.*—Slightly rough.

*Color of bark.*—RHS 200D, dark greyish reddish brown.

*Lenticels length.*—About 2.8 mm.

*Lenticels width.*—About 1.0 mm.

*Lenticels density.*—About 9 per $cm^2$ on nine year-old wood.

*Lenticels shape.*—Elliptic.

*Lenticels color.*—RHS 164B, moderate orange yellow.

Current season shoot:

*Shape in cross section.*—Round.

*Color.*—RHS 144B, strong yellow green.

*Texture.*—Smooth.

One year-old shoot:

*Length.*—Up to about 1.7 meters.

*Texture.*—Smooth.

*Internode length.*—About 16-39 mm.

*Thickness.*—Thin to medium, about 2.8-4.0 mm.

*Shape in cross section.*—Round.

*Color.*—RHS N199A, moderate olive brown.

*Anthocyanin coloration.*—Medium strength on sunny side; Upper surface: RHS 177A; Lower surface: RHS 144A.

*Intensity of arithocyanin coloration*.—Strong.
*Feathering*.—Slight to medium.
*Lenticels*.—Present.
*Lenticels density*.—About 27-29 per $cm^2$.
*Lenticels shape*.—Round.
*Lenticels length*.—About 0.6-0.8 mm.
*Lenticels width*.—About 0.6 mm.
*Lenticels color*.—RHS N167C.

Buds:
*Shape*.—Lateral: acute; Terminal: acute.
*Length*.—Lateral: About 4.9-5.9 mm; Terminal: About 5.8-6.0 mm.
*Diameter*.—Lateral: About 2.6-2.8 mm; Terminal: About 2.6-2.9 mm.
*Color*.—Lateral: RHS 200C; Terminal: RHS 200B.

Spurs:
*Shape*.—Cylindrical.
*Length*.—About 18.9-44.1 mm.
*Diameter*.—About 3.8-4.1 mm.
*Color*.—RHS 165A.
*Leaves per spur*.—About 9.77.

Mature wood:
*Color*.—RHS 165A.

Foliage:
*Density*.—Dense.

Leaf blade:
*Length*.—About 53-66 mm, average 61 mm.
*Width*.—About 18-23 mm, average 20 mm.
*Length/width ratio*.—Low to medium.
*Shape*.—Elliptic.
*Shape of base*.—Obtuse.
*Shape of apex*.—Acute.
*Color*.—Upper surface: RHS NN137B, greyish olive green.
*Incisions of margin*.—Crenate.
*Venation type*.—Arcuate to pinnate.

Petiole:
*Length*.—About 15-24 mm, average about 19 mm.
*Color*.—RHS 143B, strong yellow green.
*Shape in cross section*.—Concave.

Flower buds:
*Distribution*.—Intermediate.
*Shape*.—Conical.
*Color of tip of petals*.—RHS 62D, pale purplish pink.
*Color of sepals*.—RHS 183B, dark red.
*Hairiness of sepals*.—Strong.

Flower:
*Diameter of flower*.—About 38-45 mm, average about 42 mm, medium to large.
*Depth of flower*.—About 19.66 mm (average).
*Number of flowers*.—Single or clusters.
*Texture of flowers*.—Smooth.
*Scent of flowers*.—Moderate fragrance.
*Length of petals*.—About 20.04 mm (average).
*Width of petals*.—About 14.61 mm (average).
*Texture of petals*.—Upper surface: Velvet; Lower surface: Velvet.
*Margin*.—Indented, retuse with 2 lobes, some deep.
*Shape of petals*.—Elliptic to broad elliptic.
*Shape of apex*.—Retuse, indented.
*Shape of base*.—Acute.
*Number of petals*.—Five or six.
*Color of petals*.—Upper surface: RHS N155D, yellowish white. Lower surface: RHS N155B.
*Number of stamens*.—About 28.7 (average).
*Number of pistils*.—Always one.
*Length of pistils*.—About 13.48 mm (average).
*Color of pistils*.—RHS 150C.
*Position of stigma as compared with anthers*.—Below.

Sepals:
*Number*.—Five.
*Shape*.—Broad elliptic.
*Length*.—About 7.43 mm (average).
*Width*.—About 5.62 mm (average).
*Apex*.—Rounded.
*Margin*.—Medium hairiness.
*Color*.—Outer surface: RHS 143C with RHS 187C anthocy. Inner surface: RHS 143C.

Pedicels:
*Length*.—About 2.72 mm (average).
*Color*.—RHS 144C.

Stamen:
*Anthocyanin coloration of filament*.—White to RHS 64B when mature on lower half.
*Length of filament*.—About 8.01 mm (average).

Stigma:
*Size*.—Medium.

Pollen:
*Amount*.—Moderate.
*Color*.—RHS 153D.

Green fruit:
*Shape*.—Ovate.
*Average length*.—About 36.11 mm.
*Average width*.—About 28.32 mm.
*Average thickness*.—About 24.34 mm.
*Color*.—RHS N148B, moderate yellow green.
*Pubescence*.—Much to very much.

Dry fruit:
*Shape*.—Ovate.
*Shape of apex*.—Pointed.
*Length*.—About 30-35 mm.
*Width*.—About 23-28 mm.
*Thickness*.—About 15-18 mm.
*Average weight*.—About 4.6 g.
*Color*.—RHS 164B, moderate orange yellow.
*Surface*.—Smooth with moderate pitting.
*Thickness of endocarp*.—About 2-3 mm.
*Resistance to cracking*.—Hard.
*Percentage of kernel to dry fruit*.—Approximately 27%.
*Keel development*.—Weak.
*Distribution on tree*.—On spurs and one year-old shoots.
*Base*.—Weakly cordate.
*Color*.—Inner surface: RHS 164C.

Fruit:
*Percentage of double kernels*.—None.
*Eating quality*.—Excellent. Oil content average is about 53%; Oleic acid is about 67%, Vitamin E is about 44.2 mg/100 g oil.
*Production*.—Regular fruit bearer.

Kernel:
*Shape*.—Broad elliptic.
*Size*.—Large.
*Average weight*.—About 1.4 g.
*Length*.—About 22-26 mm.
*Width*.—About 15-18 mm.
*Thickness*.—About 7-10 mm.
*Main color*.—RHS 165B, brownish orange.
*Intensity of color*.—Light.

*Rugosity*.—Weak.

*Taste*.—Sweet.

*Apex*.—Broad short acuminate.

*Base*.—Flat.

*Yield*.—About 4,449 kg/ha at 10 years.

Blooming/flowering timing:

*Time of beginning of flowering*.—Mid-August to early September (late winter — Australia); Full bloom about one to two days after 'Nonpareil'.

*Time of leaf budburst in relation to beginning of flowering*.—After first week of September, generally occurs towards end of bloom time.

*Flowering period*.—Mid-August to early September (late winder to early spring — Australia); Up to about four weeks depending on the weather; Full bloom about mid-August.

*Time of maturity*.—Approximately 30 weeks from beginning of flowering (about 7 months from August to March — Australia).

Cultural characteristics:

*Susceptibility to disease*.—Very good tolerance to bacterial spot.

Storage/shipping:

*Storage ability*.—Good, partly because Oleic acid content is about 62%.

*Shipping ability*.—Good.

Harvest:

*Peak*.—February (late summer — Australia); Approximately 10 days after Nonpariel.

Pest resistance/susceptibility:

*Resistance*.—Hard shell is resistant to many insect attacks. Very good resistance to hull rot and bacterial spot.

We claim:

1. A new and distinct variety of almond tree (*Prunus dulcis*) named 'CAPELLA', as illustrated and described herein.

* * * * *